(12) United States Patent
Yoshikawa et al.

(10) Patent No.: US 11,145,219 B2
(45) Date of Patent: Oct. 12, 2021

(54) SYSTEM AND METHOD FOR CHANGING CONTENT BASED ON USER REACTION

(71) Applicant: SONY CORPORATION, Tokyo (JP)

(72) Inventors: Kiyoshi Yoshikawa, Saitama (JP); Naoya Sazuka, Tokyo (JP); Yoshihiro Wakita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/308,502

(22) PCT Filed: Apr. 12, 2017

(86) PCT No.: PCT/JP2017/014979
§ 371 (c)(1),
(2) Date: Dec. 10, 2018

(87) PCT Pub. No.: WO2017/221525
PCT Pub. Date: Dec. 28, 2017

(65) Prior Publication Data
US 2020/0184843 A1    Jun. 11, 2020

(30) Foreign Application Priority Data

Jun. 23, 2016  (JP) .............................. JP2016-124091

(51) Int. Cl.
| | |
|---|---|
| *G09B 19/00* | (2006.01) |
| *A61B 5/16* | (2006.01) |
| *A61B 5/021* | (2006.01) |
| *A61B 5/024* | (2006.01) |
| *A61B 5/08* | (2006.01) |

(Continued)

(52) U.S. Cl.
CPC .............. *G09B 19/00* (2013.01); *A61B 5/021* (2013.01); *A61B 5/024* (2013.01); *A61B 5/0816* (2013.01); *A61B 5/1104* (2013.01); *A61B 5/163* (2017.08); *A61B 5/4266* (2013.01); *A61B 5/4803* (2013.01); *G09B 7/02* (2013.01)

(58) Field of Classification Search
CPC .......... G09B 19/00; G09B 7/02; A61B 5/163; A61B 5/021; A61B 5/024; A61B 5/0816; A61B 5/1104; A61B 5/4266; A61B 5/4803
See application file for complete search history.

(56) References Cited

U.S. PATENT DOCUMENTS

| | | |
|---|---|---|
| 2006/0106275 A1 | 5/2006 | Raniere |
| 2007/0100214 A1 | 5/2007 | Steinert |

(Continued)

FOREIGN PATENT DOCUMENTS

| | | |
|---|---|---|
| CA | 2545243 A1 | 6/2005 |
| CA | 2616635 A1 | 2/2007 |

(Continued)

OTHER PUBLICATIONS

International Search Report and Written Opinion of PCT Application No. PCT/JP2017/014979, dated May 23, 2017, 09 pages of ISRWO.

*Primary Examiner* — Corbett B Coburn
(74) *Attorney, Agent, or Firm* — Chip Law Group

(57) ABSTRACT

Provided is an information processing apparatus including a processing unit that presents content to a user on a basis of sensor information acquired by a sensor that detects reaction of the user to a stimulus given to the user.

16 Claims, 18 Drawing Sheets

(51) Int. Cl.
*A61B 5/11* (2006.01)
*A61B 5/00* (2006.01)
*G09B 7/02* (2006.01)

(56) References Cited

U.S. PATENT DOCUMENTS

2013/0194177 A1 8/2013 Sakata
2016/0103487 A1 4/2016 Crawford et al.
2017/0365101 A1* 12/2017 Samec ............... G02B 27/0172

FOREIGN PATENT DOCUMENTS

| | | | |
|---|---|---|---|
| CN | 1882372 | A | 12/2006 |
| CN | 101232860 | A | 7/2008 |
| CN | 103181180 | A | 6/2013 |
| CN | 105051647 | A | 11/2015 |
| JP | 2001-252265 | A | 9/2001 |
| JP | 2007-512086 | A | 5/2007 |
| JP | 2009-502363 | A | 1/2009 |
| JP | 2010-244334 | A | 10/2010 |
| JP | 2012-203288 | A | 10/2012 |
| JP | 2016-513319 | A | 5/2016 |
| KR | 10-2015-0106954 | A | 9/2015 |
| WO | 2005/055802 | A2 | 6/2005 |
| WO | 2007/016471 | A2 | 2/2007 |
| WO | 2013/018267 | A1 | 2/2013 |
| WO | 2014/142962 | A1 | 9/2014 |

* cited by examiner

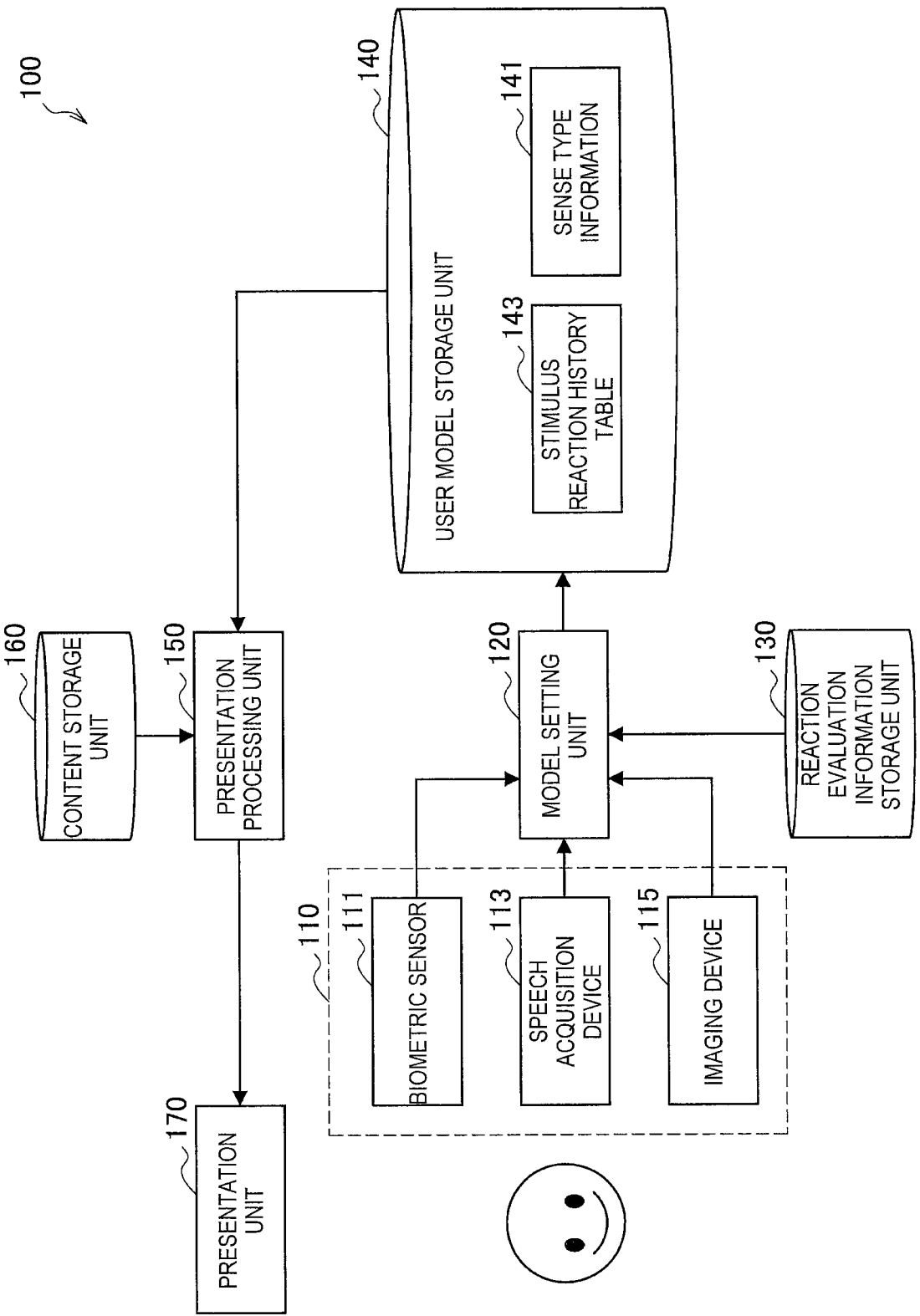

FIG. 4

| EFFECTOR (ORGAN) | | SYMPATHETIC NERVOUS SYSTEM | PARASYMPATHETIC NERVOUS SYSTEM |
|---|---|---|---|
| PUPIL | | MYDRIASIS | MIOSIS |
| SALIVARY GLAND | | SMALL AMOUNT HIGH-CONCENTRATION SALIVARY SECRETION | LARGE AMOUNT LOW-CONCENTRATION SALIVARY SECRETION |
| BRONCHIAL TUBE | | BRONCHODILATATION | BRONCHOCONSTRICTION |
| AIRWAY SECRETION | | (DROP) | (RISE) |
| BLOOD PRESSURE | | (RISE) | SLIGHT (DROP) |
| HEART RATE | | (RISE) | (DROP) |
| LIVER | | GLYCOGENOLYSIS | GLYCOGENESIS |
| GASTRO-INTESTINAL TRACT | MOTILITY | (DROP) | (RISE) |
| | SECRETION | (DROP) | (RISE) |
| SKIN | BLOOD VESSEL | VASOCONSTRICTION | — |
| | SWEAT GLAND | PERSPIRATION (RISE) | — |
| | ARRECTOR PILI MUSCLE | MUSCLE CONTRACTION | — |

FIG. 7

| SENSE TYPE | PROPORTION |
|---|---|
| VISUAL SENSE | X% |
| AUDITORY SENSE | Y% |
| TACTILE SENSE | Z% |

FIG. 8

| TIME | PLACE | SCENE | CONTENT | STIMULUS INFORMATION | | REACTION | EFFECT | |
|---|---|---|---|---|---|---|---|---|
| | | | | IMPRESSION OBJECT | STIMULUS | | EVALUATION (1-10) | GROUNDS |
| 2016/5/20 Fri. 10:00 | SCHOOL | SELF-LEARNING | ENGLISH WORD TEACHING MATERIALS | WORD | SCALE-UP | NO SPIRITUAL PERSPIRATION IN 5 MINUTES FROM START | 3 | MAKE MISTAKE IN QUIZ |
| 2016/5/20 Fri. 16:00 | LIBRARY | READING | DIGITAL PICTURE BOOK | WOLF | AROUSAL LEVEL: 4 | RISE IN HEART RATE - INCREASE IN PERSPIRATION | 7 | FROM BIOMETRIC REACTION AT STIMULUS REGULAR TIME |
| | | | | LITTLE RED RIDING HOOD | AROUSAL LEVEL: 2 | | | |
| ... | ... | ... | ... | ... | ... | ... | ... | ... |

FIG. 11

| IMPRESSION OBJECT | AROUSAL LEVEL |
|---|---|
| WOLF | 4 |
| LITTLE RED RIDING HOOD | 2 |

FIG. 12

| STIMULUS INFORMATION | | AROUSAL LEVEL | | | | |
|---|---|---|---|---|---|---|
| | | 1 | 2 | ... | 4 | 5 |
| VISUAL SENSE | MOVEMENT | +5% | +10% | ... | +20% | +25% |
| AUDITORY SENSE | SOUND EFFECTS | +2.5% | +5% | ... | +10% | +12.5% |
| TACTILE SENSE | VIBRATION | 0sec | 1sec | ... | 3sec | 4sec |

FIG. 13
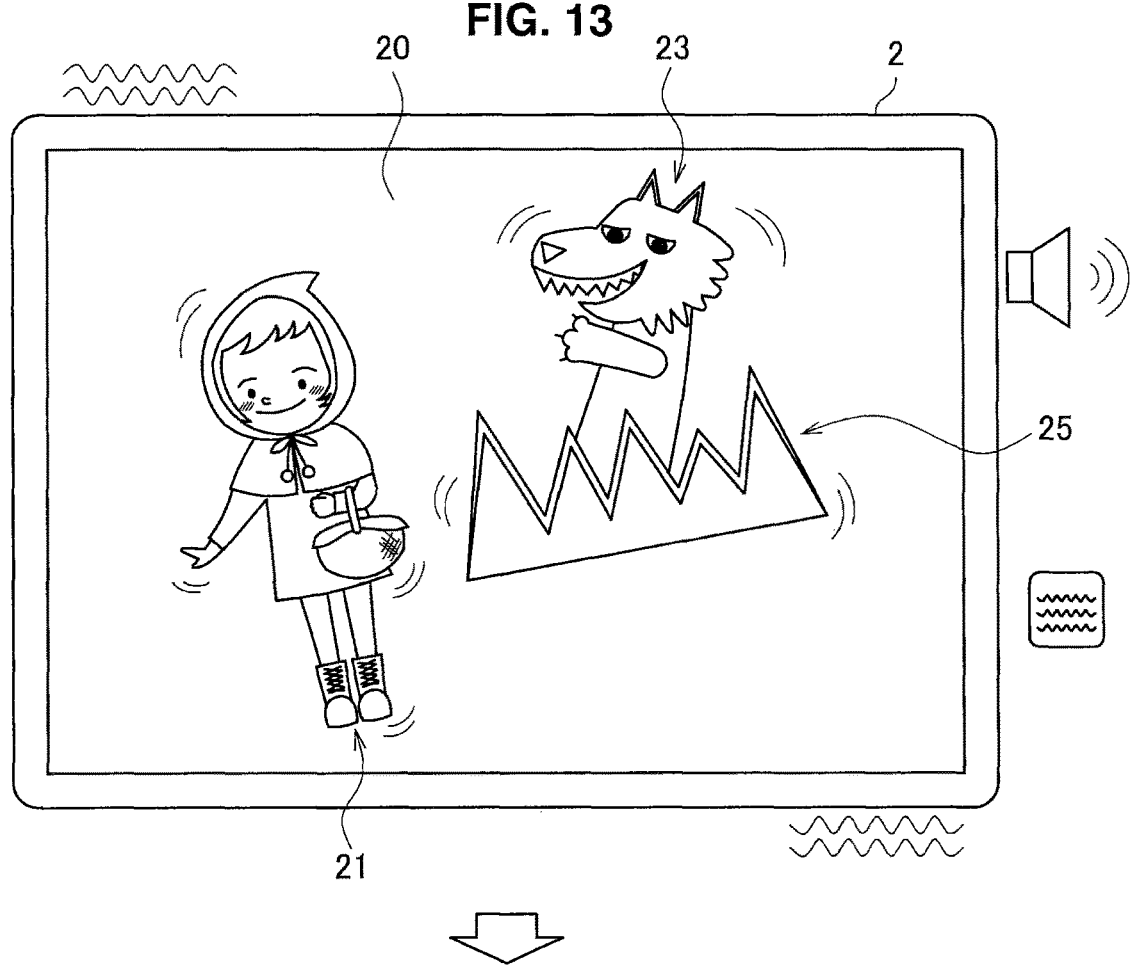
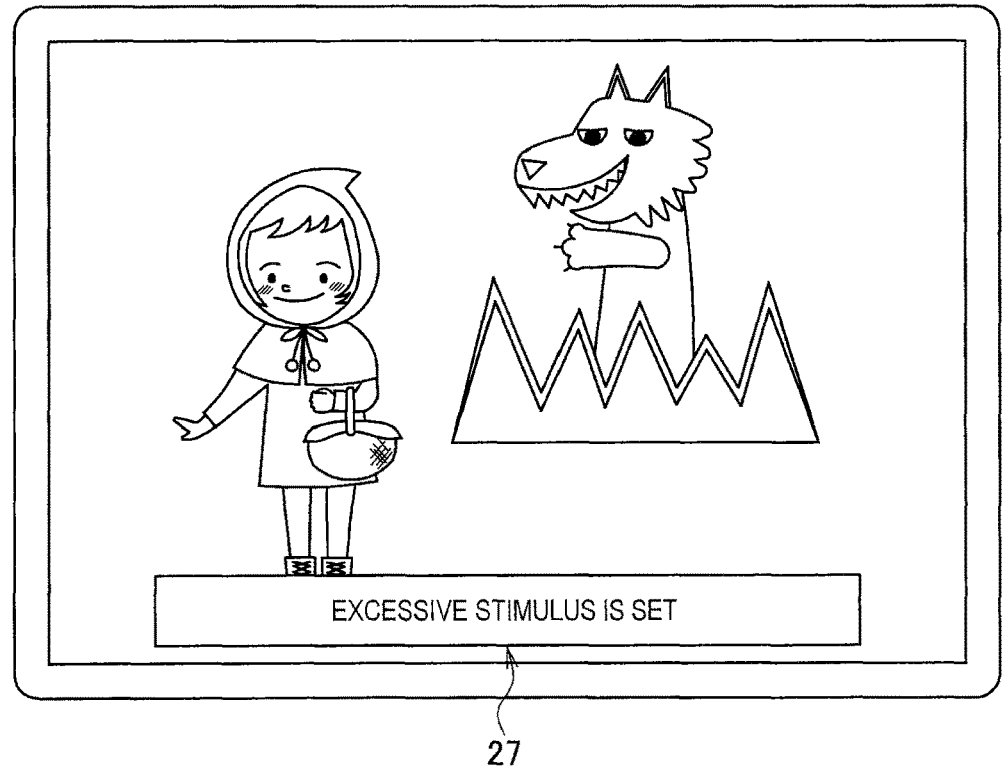

SYSTEM AND METHOD FOR CHANGING CONTENT BASED ON USER REACTION

CROSS REFERENCE TO RELATED APPLICATIONS

This application is a U.S. National Phase of International Patent Application No. PCT/JP2017/014979 filed on Apr. 12, 2017, which claims priority benefit of Japanese Patent Application No. JP 2016-124091 filed in the Japan Patent Office on Jun. 23, 2016. Each of the above-referenced applications is hereby incorporated herein by reference in its entirety.

TECHNICAL FIELD

The present disclosure relates to an information processing apparatus, an information processing method, and a computer program.

BACKGROUND ART

With widespread use of content, it is considered to present appropriate information for each user in presenting information to the user. In one example, a technique for analyzing the user's preference and presenting information suitable for the user's preference, a technique for personalizing an idea stimulus facilitating that the user generates an idea and presenting it to the user in the user's idea generation support (e.g., Patent Literature 1), or others are developed.

CITATION LIST

Patent Literature

Patent Literature 1: JP 2010-244334A

DISCLOSURE OF INVENTION

Technical Problem

Here, a human being senses external environments using five senses, namely, visual, auditory, tactile, gustatory, and olfactory senses. It is known that a human being has each sense superior to others among these senses. In one example, in receiving information presentation, there is a case where information visually presented on a screen is easier to understand than that audibly presented by voice. Thus, how to present easy-to-understand information is different depending on the person. Such a difference is thought to be related to difference in the dominance of each person's five senses.

In view of this, the present disclosure provides a novel and improved information processing apparatus, information processing method, and computer program, capable of presenting information in a presentation way that allows each user to easily accept information.

Solution to Problem

According to the present disclosure, there is provided an information processing apparatus including: a processing unit configured to present content to a user on a basis of sensor information acquired by a sensor configured to detect reaction of the user to a stimulus given to the user.

In addition, according to the present disclosure, there is provided an information processing method including: presenting content together with a stimulus; detecting, by a sensor, reaction of a user to the stimulus given to the user; and estimating a dominant sense of the user on a basis of sense information acquired by the sensor.

In addition, according to the present disclosure, there is provided a computer program causing a computer to function as an information processing apparatus including: a processing unit configured to present content to a user on a basis of sensor information acquired by a sensor configured to detect reaction of the user to a stimulus given to the user.

Advantageous Effects of Invention

According to the present disclosure as described above, it is possible to present information using a presentation way that allows each user to accept information with ease. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a functional block diagram illustrating an exemplary configuration of an information presentation system according to the present embodiment.

FIG. 4 is a diagram illustrated to describe a relationship between biometric information and user's reaction, as an example of information held by a reaction evaluation information storage unit.

FIG. 7 is a diagram illustrated to describe an example of sense type information stored in a user model storage unit.

FIG. 8 is a diagram illustrated to describe an example of a stimulus reaction history table stored in the user model storage unit.

FIG. 11 is a diagram illustrated to describe an example of magnitude of stimulus information set in an impression object.

FIG. 12 is a diagram illustrated to describe contents of stimulus information that is set for an impression object.

FIG. 13 is a diagram illustrated to describe a caution issued to a content creator in a case where stimulus information is excessively set.

MODE(S) FOR CARRYING OUT THE INVENTION

Figure 1:
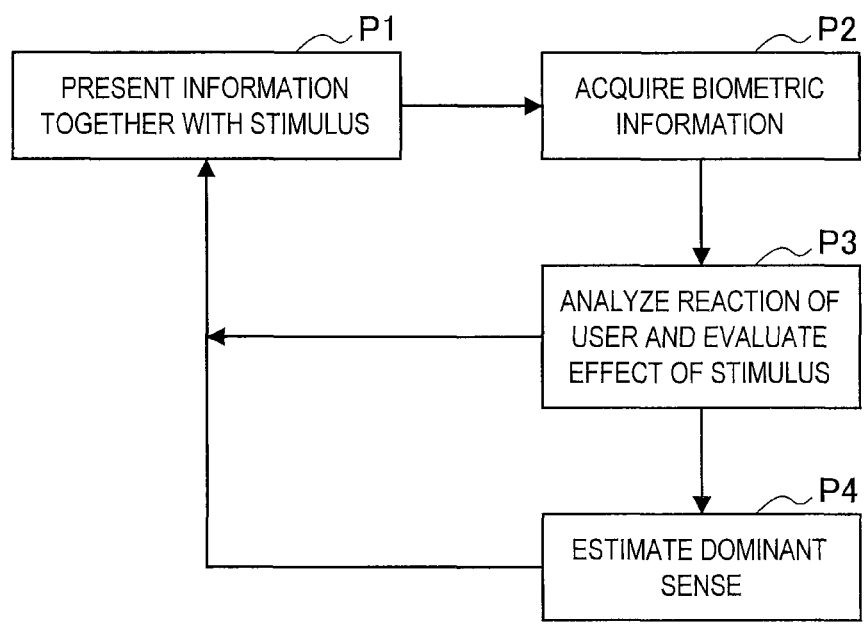
FIG. 1 is a diagram illustrated to describe an overview of content presentation using an information processing apparatus according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Moreover, the description will be given in the following order.
1. Overview
2. Configuration of information processing apparatus
3. Information presentation way
4. Use case
[Use case 1: Digital picture book]
[Use case 2: Presentation of guide information for each sense type]
[Use case 3: Digital teaching materials]
(1) English word learning method
(2) Change of content presentation depending on change in user reaction
[Use case 4: Use of estimated user model]
(1) Learning support (class division or team division)
(2) Theme park, Art gallery, and Exhibition
(3) Communication support
5. Hardware configuration
<1. Overview>

Figure 2:
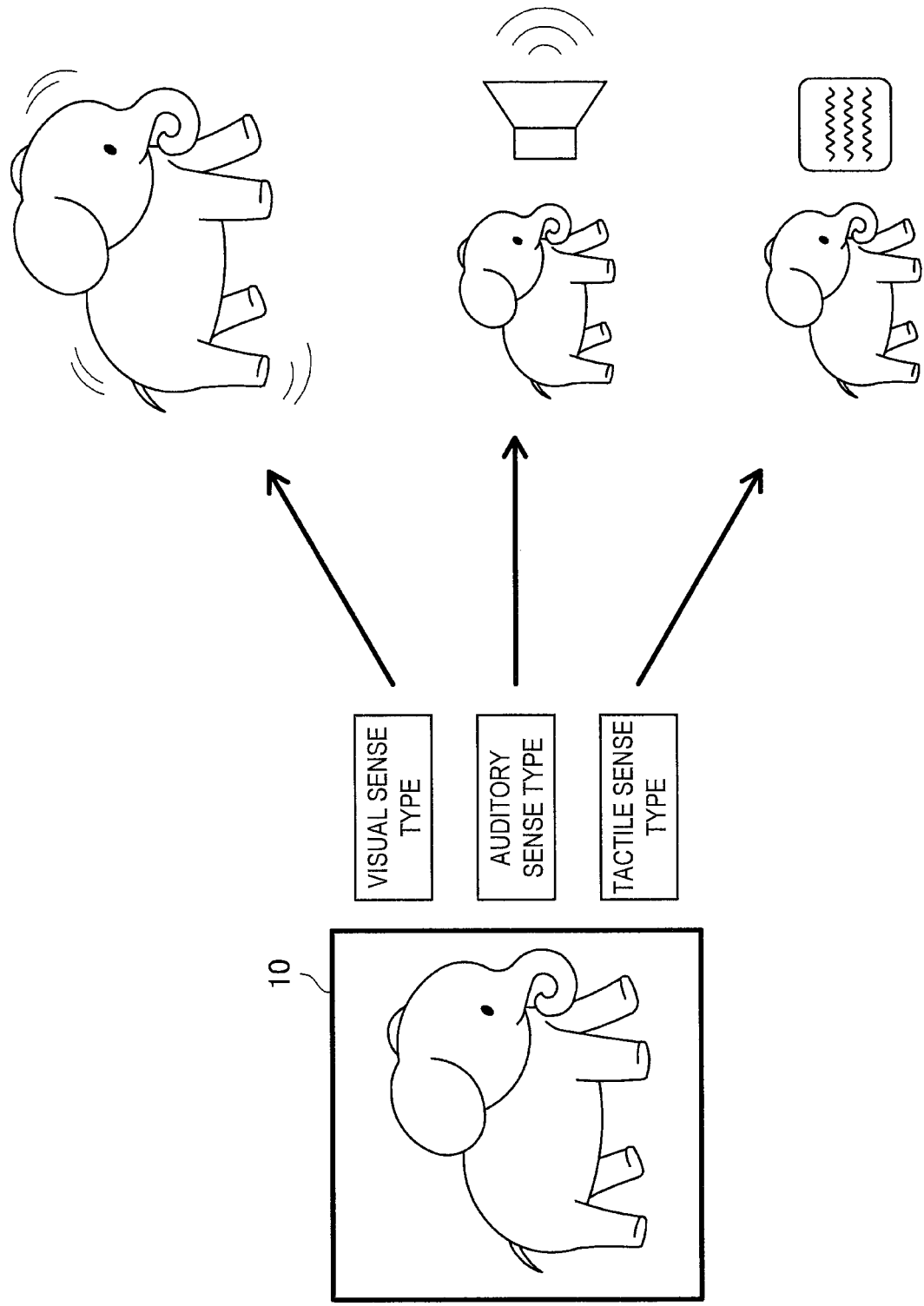
FIG. 2 is a diagram illustrated to describe an example of content presentation for each user using the information processing apparatus according to the present embodiment.

An overview of a way of presenting content by an information processing apparatus according to an embodiment of the present disclosure is now described with reference to FIGS. 1 and 2. FIG. 1 is a diagram illustrated to describe an overview of content presentation using the information processing apparatus according to the present embodiment. FIG. 2 is a diagram illustrated to describe an example of content presentation for each user using the information processing apparatus according to the present embodiment.

The information processing apparatus according to the present embodiment presents information using a presentation way that allows each user to easily accept information. This technology estimates a sense that works dominantly among the user's senses (hereinafter also referred to as "dominant sense") and presents information in such a manner to stimulate the dominant sense, so that the user accepts information without being subjected to load. It is possible to estimate the dominant sense of each user on the basis of the user's biometric information.

Specifically, as illustrated in FIG. 1, in presenting information to a user, information is presented in such a manner that a sense (e.g., visual, auditory, or tactile sense) is stimulated (P1). In this event, biometric information of the user who received the stimulus is acquired (P2). Then, the reaction of the user who received the stimulus is estimated by analyzing the acquired biometric information of the user, and whether or not the stimulus given on the basis of the user's reaction has an effect on the user is evaluated (P3). The evaluation of the process P3 is fed back to a functional unit, which presents the information, to use for consideration in presenting the information to the user later and is employed as information used to estimate a user's dominant sense from the user's reaction to the stimulus (P4). The process P4 estimates the user's dominant sense on the basis of the reactions to various stimuli presented to the user in the processes P1 to P3. The feedback of the estimated dominant sense of the user to a functional unit used to present the information allows the information to be present to the user in such a manner to stimulate the dominant sense.

In one example, as illustrated in FIG. 2, it is assumed that there is an object 10 to be impressed by a viewer (hereinafter also referred to as "impression object") among objects included in the video content. Only the addition of stimulus information is set in the video content in presenting an impression object 10. When the impression object 10 is set in the video content, the information processing apparatus sets the stimulus information in the impression object 10 on the basis of the viewer's dominant sense for the video content and plays back the video content.

Here, it is said that the way of recognizing the information differs for each user depending on the user's dominant sense. In the present disclosure, differences in information recognition depending on the user's dominant sense are represented by classifying them into sense types. Here, three sense types are set, for example, visual sense type in which visual sense works dominantly, auditory sense type in which auditory sense works dominantly, and tactile sense type in which tactual sense works dominantly. How to receive information, how to communicate it, how to store it, and so on are different depending on each sense type, and in one example, these differences appear in the body's movement.

The description is first given of the movement of eyeball as an example of the body's movement. The visual sense type user tends to have the movement of the eyeball that looks upwards or looks around restlessly. In addition, the auditory sense type user tends to move the eyes along the contents of the information while looking at one point or look downward slightly. The tactile sense type user tends to swing the eyes in the horizontal direction or downward. The description is given of the movement of hand or arm as another example of the body's movement. The visual sense type user tends to move the hand or the like upward, the auditory sense type user tends to move it according to the meaning of the story, and the tactile sense type user tends to move the arm up and down exaggeratedly.

Further, for transmission and storage of information, in many cases, the visual sense type user tends to have strong obsession about an image or color, have a logical leap in speech, or talk rapidly. Then, the visual sense type user tends to perceive the information in terms of planes and store it. In addition, the auditory sense type user tends to have obsession about time or distance and so speak consistently. Many people speak at a slow speed with less intonation of voice. Then, the auditory sense type user tends to associate information and store it in terms of lines. The tactile sense type user tends to have a lot of onomatopoeia or mimetic words and have much intonation of voices. Then, the tactile sense type user tends to store information individually in terms of points.

Thus, in the present disclosure, the user's dominant sense is estimated and information is presented to the user in such a manner to stimulate the dominant sense. In one example, in FIG. 2, it is assumed that an elephant included in the video content is impressed to the user as an impression object 10. In this event, when the user's sense type is the visual sense type, the information processing apparatus can scale up or down, move, or blink the elephant that is the impression object 10 in such a manner to stimulate the visual sense that is the dominant sense. In addition, when the user's sense type is the auditory sense type, the information processing apparatus can output its cry or sound effect in such a manner to stimulate the auditory sense that is the dominant sense as well as the display of the elephant that is the impression object 10. Furthermore, when the user's sense type is the tactile sense type, the information processing apparatus can vibrate equipment that the user touches while holding or wearing it in such a manner to stimulate the tactile sense that is the dominant sense as well as the display of the elephant that is the impression object 10. The equipment to be vibrated can be equipment itself provided with a display device, such as a tablet terminal, a smartphone, or a wearable terminal, which plays back the video content, or can be other devices than the equipment that plays back the video content. In this case, the equipment to be vibrated can vibrate upon reception of an instruction given from the equipment that plays back the video content, or can be controlled by a control server or the like used to control these devices via a network.

As described above, the change in the way of presenting the impression object 10 in the video content depending on the user's sense type makes it possible for each user to understand the information with ease, thereby making it easy to impress the impression object 10 to the user.

An information presentation system including the information processing apparatus for executing such processing and an information presentation way by using this system are now described in detail.

<2. Configuration of Information Processing Apparatus>

Figure 5:
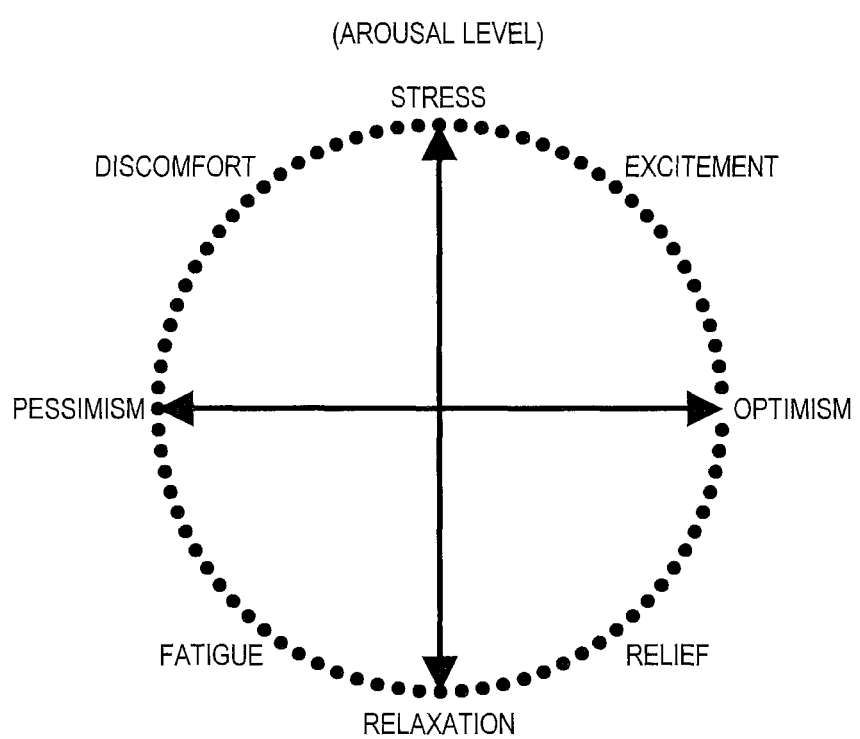
FIG. 5 is a diagram illustrated to describe an indicator used to evaluate user's reaction to a stimulus.
Figure 6:
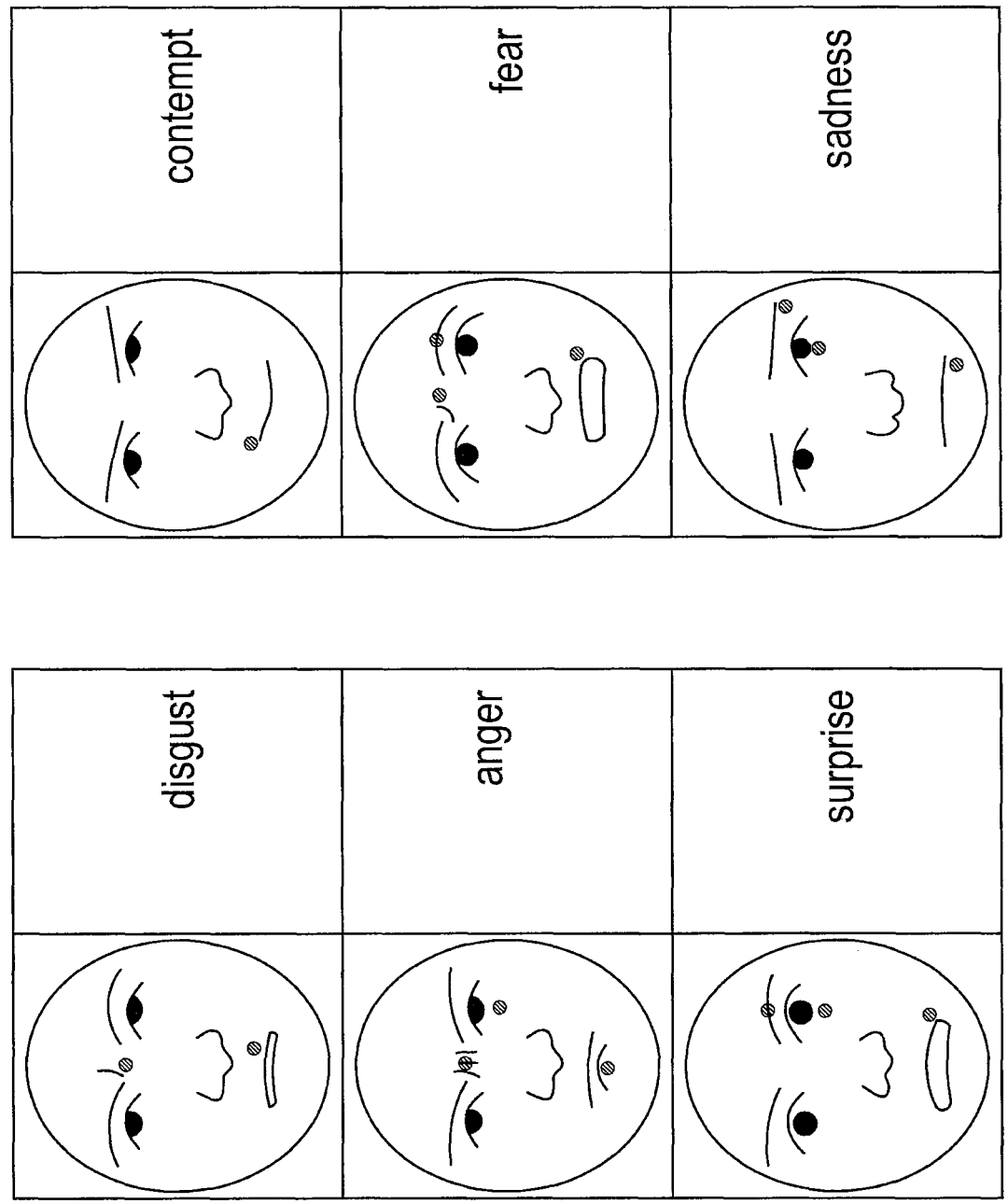
FIG. 6 is a diagram illustrated to describe an indicator in a case where user's reaction to a stimulus is evaluated from a facial expression.

The configuration of an information presentation system 100 according to an embodiment of the present disclosure is now described with reference to FIGS. 3 to 8. Moreover, FIG. 3 is a functional block diagram illustrating an exemplary configuration of the information presentation system 100 according to the present embodiment of the present disclosure. FIG. 4 is a diagram illustrated to describe the relationship between biometric information and user's reaction as an example of information held by a reaction evaluation information storage unit 130. FIG. 5 is a diagram illustrated to describe an indicator used to evaluate user's reaction to a stimulus. FIG. 6 is a diagram illustrated to describe an indicator in a case where user's reaction to a stimulus is evaluated from a facial expression. FIG. 7 is a diagram illustrated to describe an example of sense type information 141 stored in a user model storage unit 140. FIG. 8 is a diagram illustrated to describe an example of a stimulus reaction history table 143 stored in the user model storage unit 140.

The information presentation system 100 according to the present embodiment includes sensors 110, a model setting unit 120, the reaction evaluation information storage unit 130, the user model storage unit 140, a presentation processing unit 150, a content storage unit 160, and a presentation unit 170, as illustrated in FIG. 3.

The sensors 110 acquire user-related information that is used to analyze reaction of the user who receives presented information. Examples of the sensors 110 include a biometric sensor 111 for acquiring biometric information of the user, a speech acquisition device 113 for acquiring speech, and an imaging device 115 for capturing an image of the user.

The biometric sensor 111 can be, in one example, a sensor that detects a change in an organ (effector) that reacts when a user receives a stimulus from the outside as biometric information. Humans receive a stimulus such as sound or light from the external environment through receptors such as ears and eyes. The sense is stimulated when the stimulus received by the receptor is transmitted to the cerebral sensory cortex via the nervous system. Then, the cerebral motor cortex, when determining movement of the body with respect to this sense, transmits a command based on determination to the effector and activates the effector. The variation in the effector caused by this stimulus appears as reaction to the stimulus. In the present disclosure, the biometric sensor 111 detects such variation in the effector to a stimulus.

FIG. 4 illustrates an example of the effector. As illustrated in FIG. 4, examples of effectors include pupil, salivary gland, bronchial tube, airway secretion, blood pressure, heart rate, liver, gastrointestinal tract, and skin. Each effector functions in cases where the sympathetic nervous system works dominantly in stress state or the parasympathetic nervous system works dominantly in relaxation state, rather than in a case where the user feels a stimulus. In one example, the pupil is dilated, or mydriasis occurs in a case where the user feels discomfort to the stimulus received by the user and the pupil is contracted, or miosis occurs in a case where the user feels comfort to the stimulus received by the user. As described above, the effector shows variation depending on how the user feels the stimulus from the external environment. Thus, it is possible to estimate the reaction to the stimulus given to the user on the basis of value detected by the biometric sensor 111. Examples of the biometric sensor 111 include a pulse wave sensor or sphygmograph, a perspiration sensor or sweating meter, and a blood pressure meter.

Further, the speech acquisition device 113 or the imaging device 115 can be provided to function as the sensors 110. In one example, the acquisition by the speech acquisition device 113 of the user's speech when the user receives the stimulus makes it possible to perceive the intonation or magnitude of the voice, the speed of the voice, or the like. In addition, the image captured by the imaging device 115 of the user's facial expression or body's movement when the user receives the stimulus makes it possible to perceive how the user feels the stimulus on the basis of the captured still or moving image. In addition, the imaging device 115 can be used as a biometric sensor, and in one example, it is also possible to obtain a heart rate using the face-based heart rate analysis technique from the image captured by the imaging device 115 and to recognize respiration from minimal change in the body.

As described above, the sensors 110 preferably have at least one of the biometric sensor 111 or the imaging device 115, and it is possible to recognize more accurately the user's reaction as more information is acquired. The Internet-of-Things (IoT) sensors or the like can be used as the sensors 110, in addition to the biometric sensor 111, the speech acquisition device 113, and the imaging device 115. The detection values acquired by the sensors 110 are output to the model setting unit 120 as sensor information.

The model setting unit 120 sets a user model representing the user's reaction to the stimulus for each user on the basis of the sensor information. The model setting unit 120 first analyzes the sensor information and estimates the user's reaction to the stimulus presented to the user. In this event, the model setting unit 120 can estimate the user's reaction with reference to the reaction evaluation information storage unit 130 to be described later. Moreover, the reaction evaluation information storage unit 130 stores, in one example, the relationship between the biometric information and the user's reaction illustrated in FIG. 4, a two-axis mapping (FIG. 5) representing inner psychological states of the user, the relationship between the user's facial expression and emotion (FIG. 6), or the like.

In one example, the model setting unit 120 can estimate the user's reaction from variation in the effector illustrated in FIG. 4 on the basis of the biometric information acquired by the biometric sensor 111. In one example, when the user's pupil is acquired in the form of an image as the biometric information, the model setting unit 120 detects variation in the magnitude of the pupil, it is determined that the user is in stress state upon the pupil dilatation (mydriasis) and the user is in relaxation state upon the pupil contraction (miosis). In a case where there are a plurality of acquired sensor information items, the user's reaction can be estimated for each item of the sensor information. Then, the model setting unit 120 records contents of the stimulus presented to the user and the estimated user's reaction in the user model storage unit 140 as stimulus reaction history information.

Further, the model setting unit 120 evaluates the estimated user's reaction and sets the user model. The user model represents the user's dominant sense, and in one example, is represented as the user's sense type. The presentation of each information item based on the user model that is set for each user makes it possible to appropriately stimulate different dominant senses for each user, thereby allowing each user to easily accept information. The model setting unit 120 stores the set user model in the user model storage unit 140 to be described later. In addition, the model setting unit 120 can update the user model on the basis of the reaction to the stimulus given to the user.

The reaction evaluation information storage unit 130 is a storage unit that stores information used to estimate the user's reaction to the stimulus presented to the user by the model setting unit 120. The reaction evaluation information storage unit 130 can store, in one example, a circular model representing inner psychological states of the user as illustrated in FIG. 5, in addition to the relationship between the biometric information and the user's reaction illustrated in FIG. 4. In the circular model illustrated in FIG. 5, the user's reaction to the stimulus is represented as to whether the emotion is positive or negative on one axis and is represented as the excitement degree of emotion on the other axis (herein, referred to as "arousal level"). It is also possible to associate the arousal levels shown in FIG. 5 with the variation in the effector to the stimulus from the external environment illustrated in FIG. 4. The mapping by the model setting unit 120 of an emotion that is specified on the basis of on the sensor information obtained by the sensors 110 to the circular model of FIG. 5 makes it also possible to quantitatively represent the tendency of the user's reaction to the stimulus.

Further, the reaction evaluation information storage unit 130 can hold, in one example, the relationship between facial expressions and emotions as illustrated in FIG. 6. The facial expression whose corners of the mouth and outer corners of the eyes rises or falls, or the facial expression that changes due to wrinkles between the eyebrows or the like represent emotions at that time, such as disgust, anger, surprise, contempt, fear, sadness, or the like. Thus, the characteristic parts of the face forming facial expressions for various emotions are held in the reaction evaluation information storage unit 130, so the model setting unit 120 is capable of extracting the characteristic parts by analyzing the image captured by the imaging device 115 and is capable of specifying the emotion in which the extracted characteristic part appears.

Moreover, FIGS. 4 to 6 are examples of the information stored in the reaction evaluation information storage unit 130. The information presentation system according to the present disclosure does not necessarily include all of these pieces of information, or can include other pieces of information. In addition, the information stored in the reaction evaluation information storage unit 130 can be set in advance or be updated as appropriate.

The user model storage unit 140 is a storage unit that stores a user model representing the user's reaction to the stimulus. In the present embodiment, the user model storage unit 140 has user's sense type information 141 and a stimulus reaction history table 143. The sense type information 141 stores the sense type of each user estimated by the model setting unit 120 as a user model. In the sense type information 141, in one example, the proportion of each of visual, auditory, and tactile sense types is included for each user, as illustrated in FIG. 7. Some people have one sense that works dominantly, and others have multiple senses that work dominantly in the same degree. Thus, as illustrated in FIG. 7, the representation of the extent to which each sense type dominantly works as the proportion makes it possible to set a stimulus more suitable for each user. The sense type information 141 is a sense type estimated on the basis of the information stored in the stimulus reaction history table 143.

Further, the stimulus reaction history table 143 stores information such as contents presented by the information presentation system 100, stimulus information that is set, reaction of the user to the stimulus information, effect on the user, and the like. An exemplary configuration of the stimulus reaction history table 143 is illustrated in FIG. 8. The stimulus reaction history table 143 illustrated in FIG. 8 can store time, place, scene, content, stimulus information, user's reaction, and effect on the user. Information other than those illustrated in FIG. 8 can also be stored in the stimulus reaction history table 143. In addition, there can be information that is incapable of being acquired depending on the scene. In this case, it can be recorded as being unavailable or not acquired.

Examples of information stored in the stimulus reaction history table 143 are shown below.

[Time Information]
  Date and day of week of content presentation
  Elapsed time from content use start
[Place and Scene (Use Scene)]
  Place of use: home, school, friend's house, library, train, etc.
  Person who received content presentation: person in question, brothers, parents, friends, teachers, etc.
[Content]
  Type of content used: digital picture book, English words teaching materials, etc.
[Stimulus Information]
  Contents of stimulus instructed by content creator: impression object and magnitude of stimulus
  Contents of stimulus: (stimulus decision guideline) most effective stimulus, stimulus not recently used, etc.
  (actually presented stimulus) move 10% in visual sense type, give sound effect 5% in auditory sense type, etc.
  more specific stimulus presentation contents
[User Reaction]
  Reaction from sensor information of biometric sensor: increase in heart rate, increase in perspiration, increase in respiration rate, etc.
  Reaction based on information acquired by speech acquisition device and imaging device Position information in circular model of emotion: (x, y)=(Nx, Ny)

[Effect on User]

Evaluation and its grounds

E.g.) 10-stage evaluation: 7, grounds: from biometric reaction at stimulus presentation 10-stage evaluation: 3, grounds: made mistake in quiz The effect on the user caused by giving the stimulus stored in the stimulus reaction history table 143 can be updated later. In one example, it is assumed that a stimulus is added to cause a user to remember English words in using the content of English words teaching materials. There may be a case where the presented stimulus is considered to have an effect on the user because the user reacts to be effective at first glance, but thereafter, when the quiz is carried out, it is found that the user does not understand at all. In this case, the presented stimulus can be considered to be updated as having no effect in practice.

The information held by the user model storage unit 140 is appropriately updated by the model setting unit 120. In one example, it can be updated in real time every time there is reaction to a stimulus, or can be updated in a batch process after a certain period of time. In addition, the presentation processing unit 150 to be described later refers to the user model storage unit 140 and sets a stimulus to the impression object included in the content.

The presentation processing unit 150 presents various pieces of content stored in the content storage unit 160 to the user through the presentation unit 170. The presentation processing unit 150 sets a stimulus for the impression object included in the content stored in the content storage unit 160 on the basis of the information stored in the user model storage unit 140 and outputs it to the presentation unit 170. In one example, the presentation processing unit 150 can determine stimulus information to be set on the basis of the sense type information 141 in referring to the user model storage unit 140. In addition, the presentation processing unit 150 can, in one example, refer to the stimulus reaction history table 143, extract history information relating to the current stimulus from the previous stimulus content and the history of the reaction, and check the reaction to the stimulus and its effect on the basis of the extracted information. Then, the presentation processing unit 150 can determine stimulus information to be set currently. In addition, the presentation processing unit 150 can set, in one example, the stimulus information on the basis of user characteristics such as user's preference or user information set by the user, in addition to the user model.

The content storage unit 160 is a storage unit that stores content to be presented to the user. The content storage unit 160 can be provided in the same equipment or server as the presentation processing unit 150, or can be content held on the cloud. The content is not particularly limited, but content that can add a stimulus to the user in presenting the content can be assumed. In addition, examples of the content include digital content. In one example, educational content such as learning drills, book content such as digital picture books, AR content provided by synthesizing and displaying images in real time on real video, or the like is applicable.

The presentation unit 170 presents content to the user together with the stimulus that is set in the impression object. The presentation unit 170 includes, in one example, a display unit that displays information, a sound output unit that outputs sound, a vibration generation unit that vibrates equipment, and the like. Moreover, the content and the stimulus that is set in the impression object are not necessarily presented from the same equipment. In one example, in the case of imparting vibration together with presentation of the impression object, the content including the impression object is displayed on a tablet terminal, and another device such as a wristband terminal or smartphone can be vibrated in synchronization with display of the impression object.

<3. Information Presentation Way>

Figure 9:
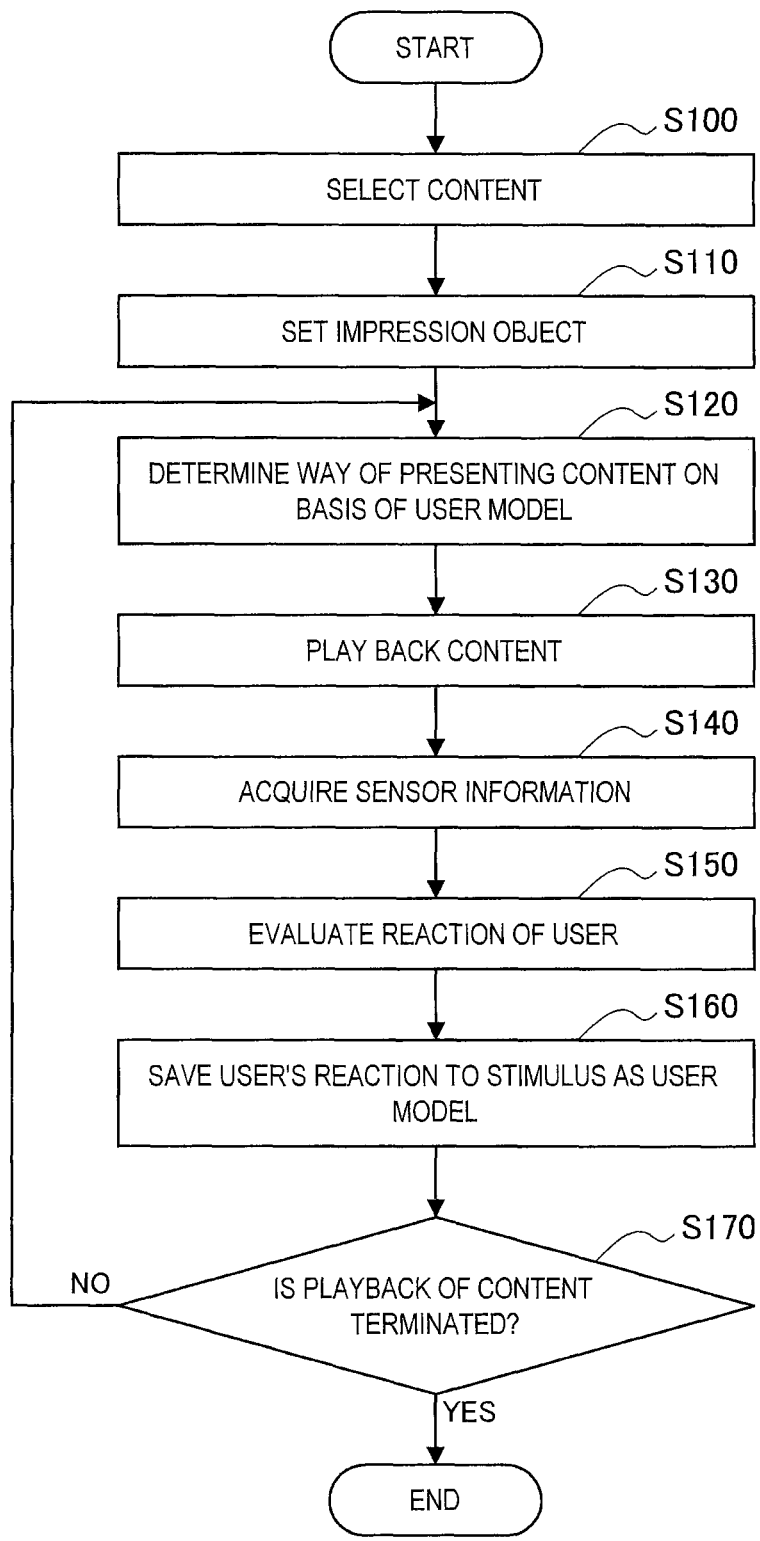
FIG. 9 is a flowchart illustrating an example of a way of presenting information performed by the information presentation system according to the present embodiment.

A basic way of presenting information performed by the information presentation system 100 illustrated in FIG. 3 is illustrated in FIG. 9. FIG. 9 is a flowchart illustrating an example of an information presentation way performed by the information presentation system 100 according to the present embodiment.

In the information presentation system 100 according to the present embodiment, a content creator first selects content to be presented to the user (S100). In this event, an object to be impressed to the user in the content is set as an impression object (S110). Steps S100 and S110 are stages for content creation before the content is provided to the user. The content creator does not necessarily set specific movement, speech, or the like for the impression object, but can set only an impression object impressed to the user.

When content whose impression object is set by the content creator is available to the user, the user is able to acquire and use the content. When the user starts using the content, the presentation processing unit 150 of the information presentation system 100 refers to the user model storage unit 140 and determines a way of presenting the content (S120). In one example, the presentation processing unit 150 refers to the sense type information 141 of the user model storage unit 140 and sets stimulus information corresponding to the sense type of the user who uses the content. In one example, in the case where the user is a visual sense type user, the impression object is displayed by scaling or blinking it. When the content presentation way is determined in step S120, the content is played back (S130), and the content is presented to the user. In presenting the impression object, the stimulus information being set is also presented together.

During the content is being presented, biometric information, facial expression, speech, or the like of the user is acquired by the sensors 110 (S140). The sensor information acquired by the sensors 110 is output to the model setting unit 120. The model setting unit 120 refers to the reaction evaluation information storage unit 130, evaluates the user's reaction when the stimulus is given, and estimates a sense type (S150). The model setting unit 120 records the presented content, the impression object, the set stimulus information, the user's reaction to the stimulus, the effect on the user of the stimulus, or the like in the stimulus reaction history table 143, and updates the sense type information 141 with the sense type estimated currently (S160). The processing from step S120 to SS160 is performed, in one example, until the playback of the content ends (S170).

The basic information presentation way performed by the information presentation system 100 is described above. Such an information presentation way makes it possible to allow the information to be presented for each user in the most acceptable manner. In addition, it is possible to implement automatically an appropriate stimulus way corresponding to the user, so the content creator does not necessarily set a detailed stimulus presentation way in giving the expected stimulus to the impression object.

Moreover, when the user's reaction to the stimulus is not obtained, in one example, a preset fixed user model or a general user model can be set in the user model storage unit 140 as an initial user model. The fixed user model is not particularly limited, and any optional initial value can be set, in one example, by setting the sense type to only "visual sense type". The general user model can be, in one example, an average value of sense type information of other users acquired previously. Alternatively, before presenting the actual content to the user, content for test used to specify an approximate sense type can be presented to set the initial user model. In this event, the reaction of the user is evaluated on the basis of the sensor information acquired when the test content is presented, and the sense type of the user is estimated. In this manner, the execution of the test processing for setting the user model of the user allows the stimulus information suitable for the user's sense immediately after the start of the content playback to be presented.

<4. Use Case>

The use case of the information presentation system according to the present embodiment is now described.

[Use Case 1: Digital Picture Book]

Figure 10:
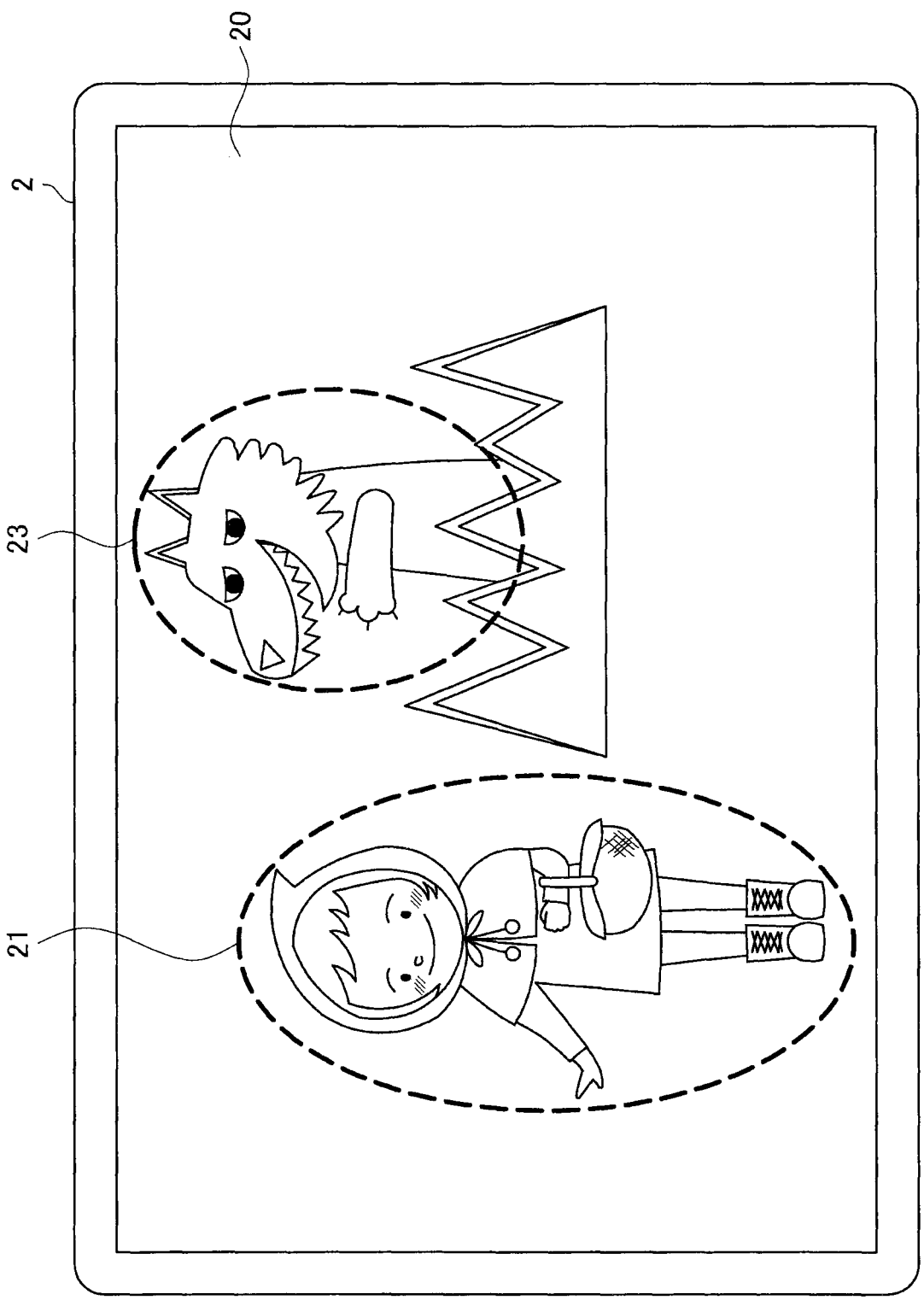
FIG. 10 is a diagram illustrated to describe, as a use case 1, an image of a digital picture book presented as content.

A case where the information presentation system 100 according to the present embodiment presents a digital picture book as content is now described with reference to FIGS. 10 to 13. Moreover, FIG. 10 is a diagram illustrated to describe an image of a digital picture book presented as content. FIG. 11 is a diagram illustrated to describe an example of the magnitude of stimulus information to be set in the impression object. FIG. 12 is a diagram illustrated to describe contents of the stimulus information to be set for the impression object. FIG. 13 is a diagram illustrated to describe a caution issued to a content creator in a case where the stimulus information is set excessively.

In the use case described herein, it is considered to, in playing back a digital picture book, set the stimulus information in people, animals, and objects appearing in the story of the digital picture book, and make the digital picture book fun and easy to remain in the user's impression. The content of a digital picture book is typically used by displaying a still or moving image on a display 20 of a terminal 2, such as a tablet terminal, as illustrated in FIG. 10. In one example, it is assumed that the digital picture book of "Little Red Riding Hood" is set by a content creator as an impression object to impress the user with the appearance of Little Red Riding Hood 21 and Wolf 23. In this event, the content creator sets an arousal level indicating the magnitude of the stimulus for each impression object. The greater the arousal level, the greater the stimulus. In one example, in the example illustrated in FIG. 11, the arousal level of Wolf is set to 4, and the arousal level of the Little Red Riding Hood is set to 2.

The presentation processing unit 150 of the information presentation system 100 refers to the sense type information 141 of the user model storage unit 140 and sets a stimulus to be given along with the content on the basis of the sense type of the user and the set arousal level of the impression object. FIG. 12 illustrates an example of setting stimulus information and arousal level. Such information can be stored in the user model storage unit 140. In FIG. 12, the magnitude of movement of the impression object is set as the stimulus to the visual sense type user, the magnitude of the effect sound is set as a stimulus to the auditory sense type user, and the vibration time of the terminal 2 is set as a stimulus to the tactile sense type user. In this example, a user who uses the digital picture book has all characteristics of visual, auditory, and tactile sense types, but the visual sense type is more dominant than the other types, so the content is presented in such a manner that the movement of the impression object is emphasized more than other stimuli.

The presentation processing unit 150 moves Wolf 23 of the arousal level 4 by 20% more than normal movement, outputs the sound effect with volume 10% higher than normal volume, vibrate the terminal 2 for three seconds, on the basis of the relationship between the stimulus information and the arousal level illustrated in FIG. 12. On the other hand, the stimulus that is set to Little Red Riding Hood 21 of the arousal level 2 is smaller than Wolf 23, moves by 10% more than normal movement, outputs the effect sound with the volume 5% higher than normal sound, and vibrates the terminal 2 for one second. In this manner, the content creator automatically sets the specific movement of the impression object only by setting of the impression object and the magnitude of the stimulus.

Here, the content creator can set the arousal level for the impression object, so there is also the possibility of setting unintended stimulus and distracting the user's attention to the impression object. In one example, as shown in the upper portion of FIG. 13, it is assumed that the stimulus information is set on a bush 25 in addition to Little Red Riding Hood 21 and Wolf 23 that are impression objects, and the movement or sound effect of each object and the vibration of the terminal 2 exceed a predetermined level. The determination as to whether or not excessive stimulus is set is performed depending on whether the number of objects for which stimulus information is set among impression objects displayed at the same time is equal to or more than a predetermined number and whether each arousal level is equal to or more than 4. In the case where excessive stimulus is set, when the content creator checks the creation details, in one example, as shown in the lower portion of FIG. 13, the user can be notified by displaying a message 27 indicating that excessive stimulus is set on the display 20, outputting sound, or the like.

[Use Case 2: Presentation of Guide Information for Each Sense Type]

Figure 14:
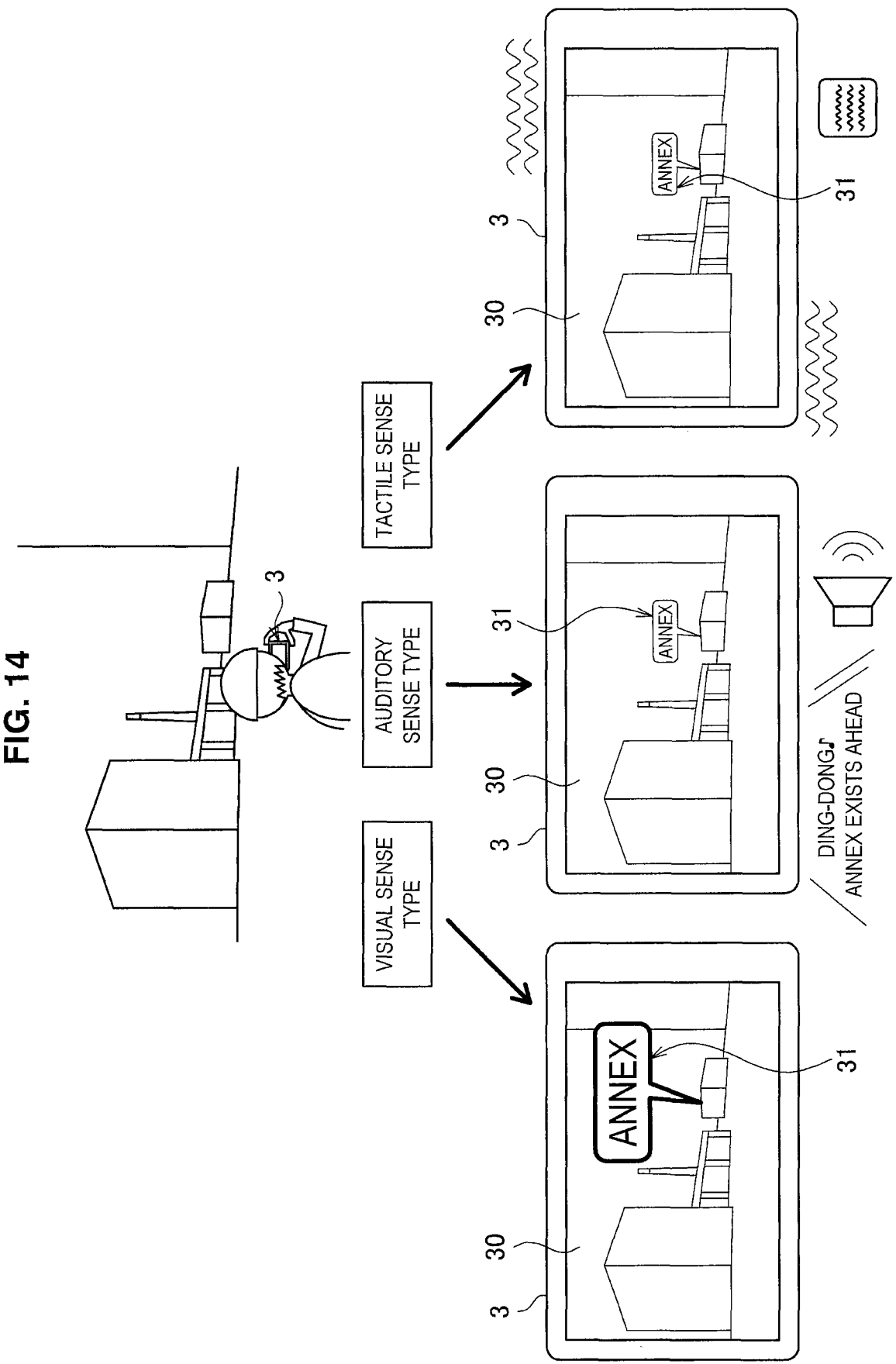
FIG. 14 is a diagram illustrated to describe, as a use case 2, an example of presenting guide information corresponding to a user's sense type.

A case where guide information using AR as content is presented by the information presentation system 100 according to the present embodiment is now described with reference to FIG. 14. FIG. 14 is a diagram illustrated to describe an example of presenting guide information corresponding to the sense type of the user. Here, an example in which the guide information using AR superimposed on the real image being displayed is suitably presented depending on the sense type of the user is illustrated. The guide information corresponds to the impression object. In this event, in addition to a smartphone or a tablet terminal, a head mounted display, an eyewear terminal, or the like can be used as a terminal 3 on which the real image and the guide information are displayed.

In the example illustrated in FIG. 14, guide information used to guide the user to an annex is presented. In this event, the content creator sets only a place where the user makes a destination as the impression object. When the user instructs the terminal 3 for guidance to the annex, the presentation processing unit 150 of the information presentation system 100 refers to the user model storage unit 140 to acquire the sense type of the user. Then, the guide information is presented depending on the sense type of the user. In one example, a guide object 31, which indicates visually the position of the annex displayed on the display 30, is highlighted and displayed to the visual sense type user. In one example, the guide object 31 is displayed on the display 30 to be smaller than the case where the guide object 31 is presented to the visual sense type user, but the position of the annex is notified by sound to the auditory sense type user. Furthermore, in one example, the guide object 31 is displayed on the display 30 to be smaller as in the case of the auditory sense type user, but the position of the annex can be notified to the tactile sense type user by vibrating the terminal 3 in the case where the annex is displayed in the display 30.

Further, it is also possible to estimate a dominant sense of the user from the behavior of the user at the time of stopping the presentation of the guide information. In one example, as processing of stopping the presentation of guide information, three actions are set, that is, winking after checking the guide, "OK" after checking the guide, and pointing the finger after checking the guide. In any of these actions, the presentation of the guide information is similarly stopped, but it can be assumed that the action selected by the user is naturally selected by the dominant sense. In one example, it can be determined that the user is the visual sense type user in the case where the user winks after checking the guide, the user is the auditory sense type user in the case where the user says "OK" after checking the guide, and the user is the tactile sense type user in the case where the user points to a finger after checking the guide. It is possible to use such actions to estimate the sense type of the user by holding the actions in the user model storage unit 140.

[Use case 3: Digital teaching materials]

A case of presenting a learning digital teaching material by the information presentation system 100 according to the present embodiment is now described.

(1) English Word Learning Method

Figure 15:
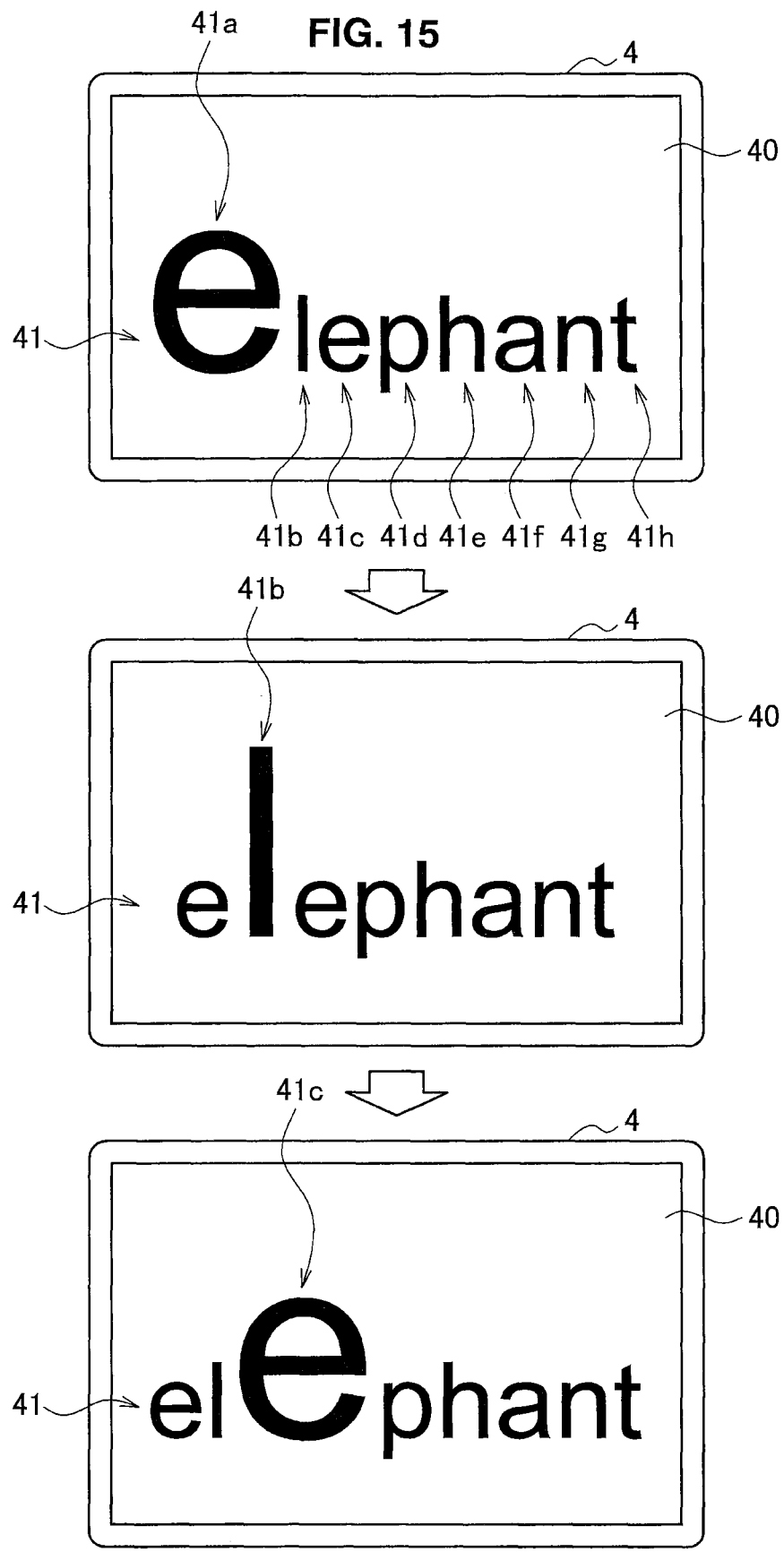
FIG. 15 is a diagram illustrated to describe, as a use case 3, an example of presenting a word to a visual sense type user.
Figure 16:
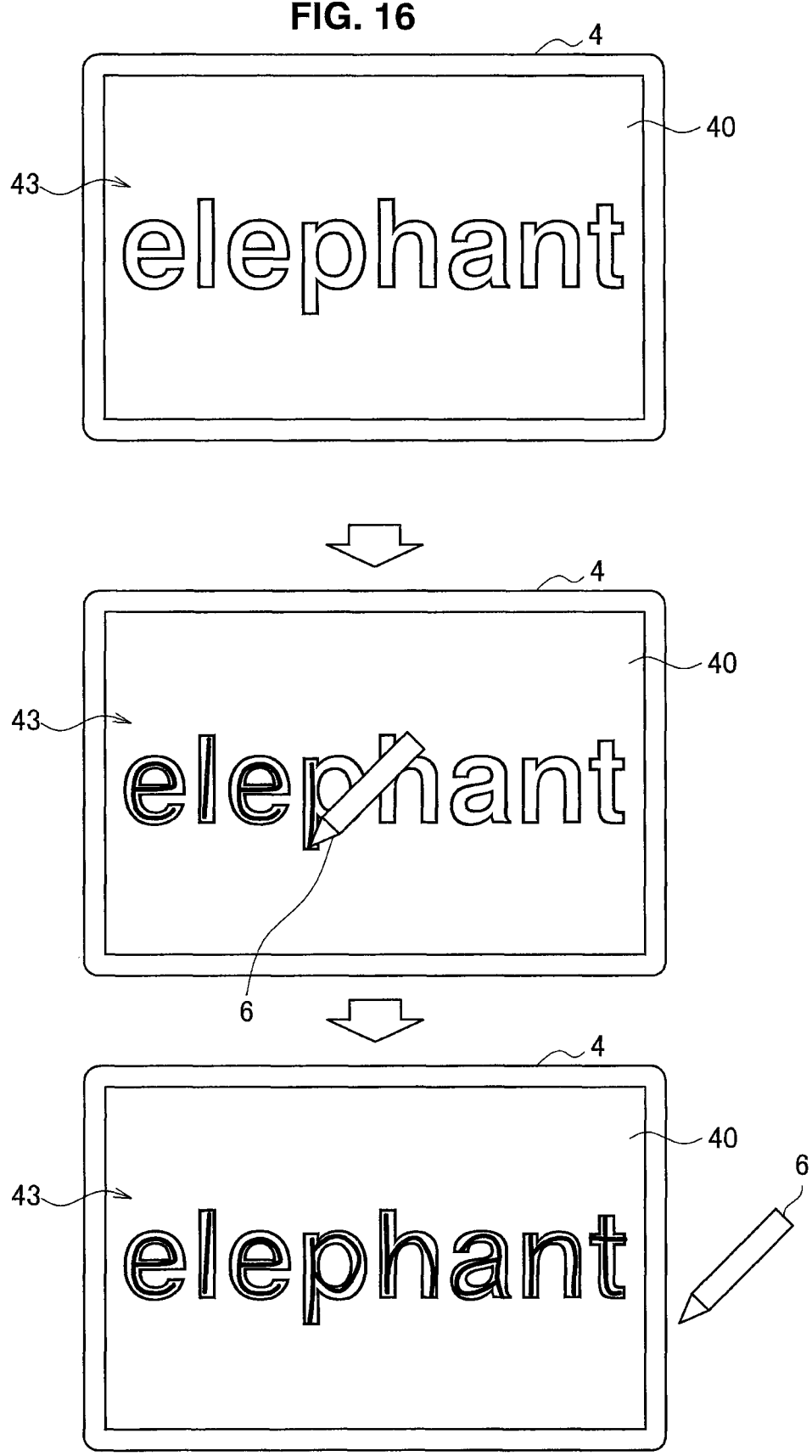
FIG. 16 is a diagram illustrated to describe an example of presenting a word to a tactile sense type user.

A case where English word teaching materials are presented as content by the information presentation system 100 according to the present embodiment is now described with reference to FIGS. 15 and 16. FIG. 15 is a diagram illustrated to describe an example of presenting words to the visual sense type user. FIG. 16 is a diagram illustrated to describe an example of presenting words to the tactile sense type user. This use case presents English words in such a manner that the user can easily remember English words in remembering English words using English word teaching materials. Here, the English word is the impression object, and in FIGS. 15 and 16, the English word "elephant" is an impression object 41.

When the user starts to learn English words using a tablet terminal 4, the presentation processing unit 150 refers to the user model storage unit 140 to acquire the sense type of the user. Then, an English word that is the impression object 41 is presented depending on the sense type of the user. In one example, for the visual sense type user, an English word "elephant" is displayed on the display 40, and alphabets 41*a* to 41*h* that constitute the word are displayed in such a manner that each character differs from other alphabets. In one example, in the example of FIG. 15, characters "e", "l", "e", . . . are displayed from the left while enlarging sequentially each character. When the character is enlarged, the color of the character can be changed.

Further, in one example, for the auditory sense type user, the English word "elephant" is displayed on the display 40. It can be played back as "E-L-E-P-H-A-N-T, ELEPHANT" by speech. Furthermore, in one example, for the tactile sense type user, as shown in the upper portion of FIG. 16, the English word "elephant" is initially displayed in a thin form on the display 40. This is referred to as a draft object 43. Then, the user is caused to trace the draft object 43 displayed on the display 40 with an operation object, such as a touch pen 6 or a finger, and to write the English word.

As described above, the use of the information presentation system 100 according to the present embodiment makes it possible to change the presentation of English words depending on the user's sense type, thereby presenting the information in a way that the user can remember easily.

(2) Change of Content Presentation Depending on Change in User Reaction

In a case where a digital teaching material is used for user self-learning, appropriate stimulus information given depending on the sense type of the user makes it possible to be expected to improve memory ability or sustained concentration. In addition, it is said that not only stimuli having good compatibility but also various stimuli are given to the user, so the brain is activated and the memory ability is improved. Thus, in the digital teaching materials, it is possible for an important part or a key point to use the stimulus having high compatibility corresponding to the user's sense type, and for other parts to use other stimuli. In this manner, the balance given to the way of presenting information for each user makes it possible to support effectively the activation of the brain. In addition, in some cases, the user's reaction is weakened for all stimuli. Conversely, it may be sensitive for minor stimuli. In such a case, the balance is given in the learning itself, in one example, by offering a rest, thereby making the learning efficient.

Figure 17:
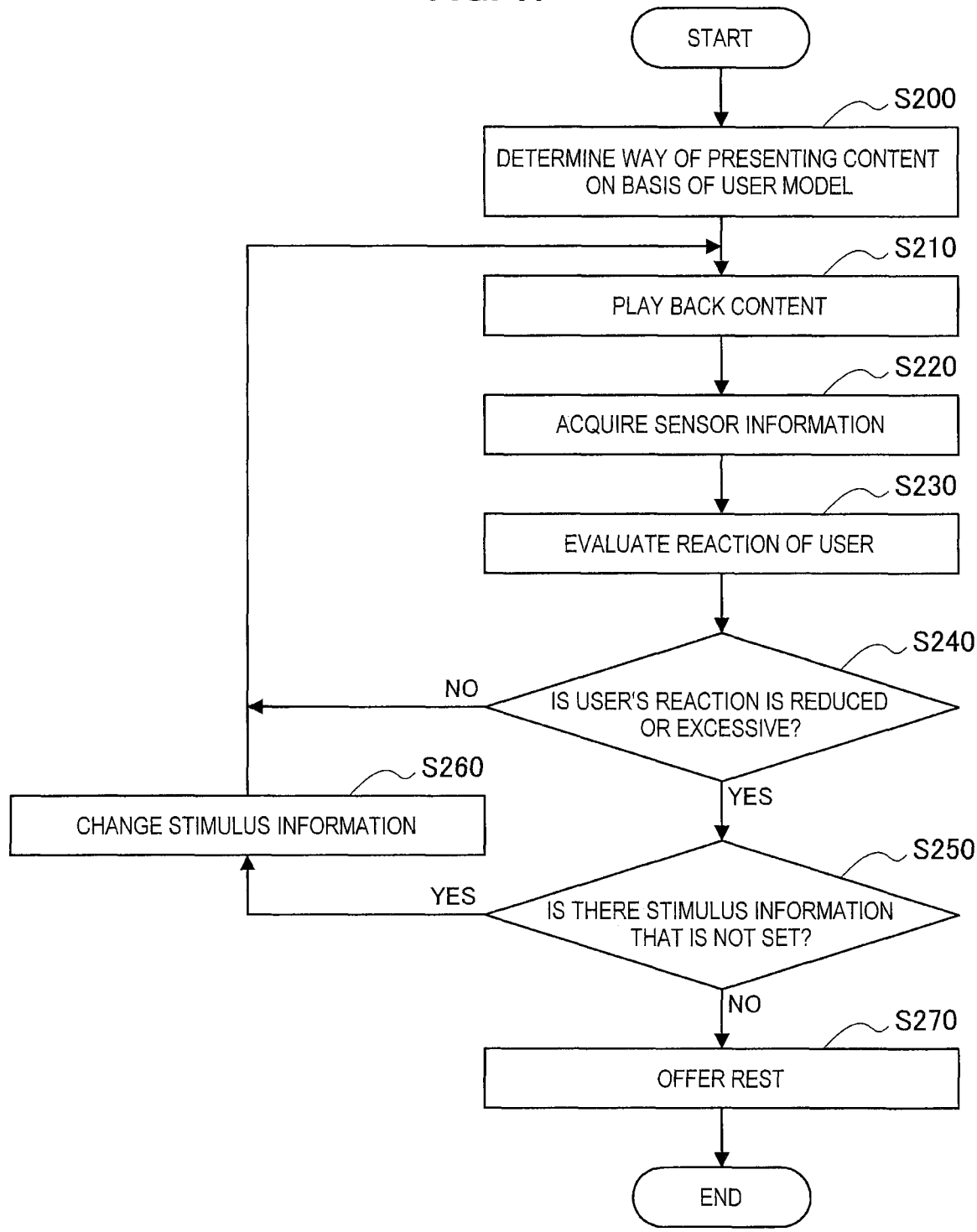
FIG. 17 is a flowchart illustrating an example of processing in a case of changing the way of presentation of content depending on a change in user's reaction.

FIG. 17 illustrates an example of processing in the case of changing the way of presentation of content depending on a change in the user's reaction. When the user starts using the content, the presentation processing unit 150 of the information presentation system 100 refers to the user model storage unit 140 and determines the way of presentation of content (S200). In one example, the presentation processing unit 150 refers to the sense type information 141 of the user model storage unit 140 and sets stimulus information corresponding to the sense type of the user who uses the content. When the content presentation way is determined in step S200, the content is played back (S210), and the content is presented to the user. In presenting an impression object, the set stimulus information is also presented.

When the content is being presented, the sensors 110 acquire biometric information, facial expression, speech, or the like of the user (S220). The sensor information acquired by the sensors 110 is output to the model setting unit 120. The model setting unit 120 refers to the reaction evaluation information storage unit 130, evaluates the user's reaction when the stimulus is given, and estimates the sense type (S230). Here, the model setting unit 120 determines whether the user's reaction is lower than a level at the time when the learning has continued so far by a predetermined ratio or is higher than the level (S240). In one example, when the user's concentration ability expires, the spiritual perspiration disappears. The determination in step S240 can be performed by utilizing such a change that the degree of change in biometric information is reduced.

In a case where the condition in step S240 is not satisfied and the user's reaction does not change so much, the processing returns to step S210 to continue the learning. On the other hand, in a case where the condition in step S240 is satisfied and the user's reaction is decreased or excessive, the presentation processing unit 150 determines whether or not there is stimulus information that is not set so far (S250). In the case where there is stimulus information that is not set, the presentation processing unit 150 changes the stimulus information at the time of presenting the impression object in anticipation of improving the user's reaction (S260), returns to step S210, continues the learning. On the other hand, in the case where there is no stimulus information that is not set in step S250, the presentation processing unit 150 offers a rest or taking a deep breath to the user to have balanced learning itself (S270).

Such a content presentation way allows what the user has learned to be kept as a record not only in the scale of time but also in terms of the quality of how much concentration to learn. In addition, for the learning contents to be an impression object of the content, the degree of stimulus information can be changed depending on the user's proficiency level. In one example, the stimulus information of a high level of proficiency is set to be weak and the stimulus information of a low level of proficiency is set to be strong in the digital teaching materials, so it is possible to give much impression to a portion that is not fixed to the user's memory. The degree of proficiency of the user can be determined, in one example, by evaluation based on the result of the quiz, the number of times of content playback, or the like.

Furthermore, it is also possible to perceive the trend of how to proceed with learning by recording the learning situation of the user for a certain period of time. In one example, at the time of learning, some users who present an answer example and then solve exercises are fewer burdens, but some users who solve exercises and then present an answer example are fewer burdens. Thus, the quantitative evaluation of the reaction in the learning process for each user and comparison between the reactions depending on the difference in the learning process allow the learning process with learning in which the user is easy to fix the learning content to be determined. This makes it possible to lower the learning load of the user and make it efficient to learn.

[Use Case 4: Use of Estimated User Model]

(1) Learning Support (Class Division or Team Division)

The information presentation system 100 according to the present embodiment makes it possible to specify the user model such as the sense type of the user. Thus, students of the same type are organized into the same class or the same team on the basis of the user model of the specified user, so a teacher can teach the class according to the type of the students. It is possible to take a lesson according to the specified sense of the students, so the degree of comprehension of the learning contents increases, thereby taking an efficient lesson. In addition, in appointing teachers, a teacher having a type that matches the type of students can be appointed, so it is expected that the teacher and students can communicate with each other in unconscious portions, and their communications can be performed satisfactorily.

(2) Theme Park, Art Gallery, and Exhibition

Further, the use of the user model that can be specified by the information presentation system 100 according to the present embodiment makes it possible to select and adjust a stimulus that is easy for a user to receive at a theme park, an art gallery, an exhibition, or the like. In one example, as the production of an attraction, in the theme park, stimulus information that is more likely to be interested is set depending on the sense type of each user, such as entering from sound for an auditory sense type person or entering from light for a visual sense type person.

(3) Communication Support

Furthermore, the information presentation system 100 according to the present embodiment is capable of specifying the user model, so it is possible to perceive the type of the partner in advance at the time of communicating with the person who is meeting for the first time, thereby making it easy to communicate. In one example, in the translation system, a translation presentation way corresponding to the sense type of the partner or its effect can be set as stimulus information.

<5. Hardware Configuration>

Figure 18:
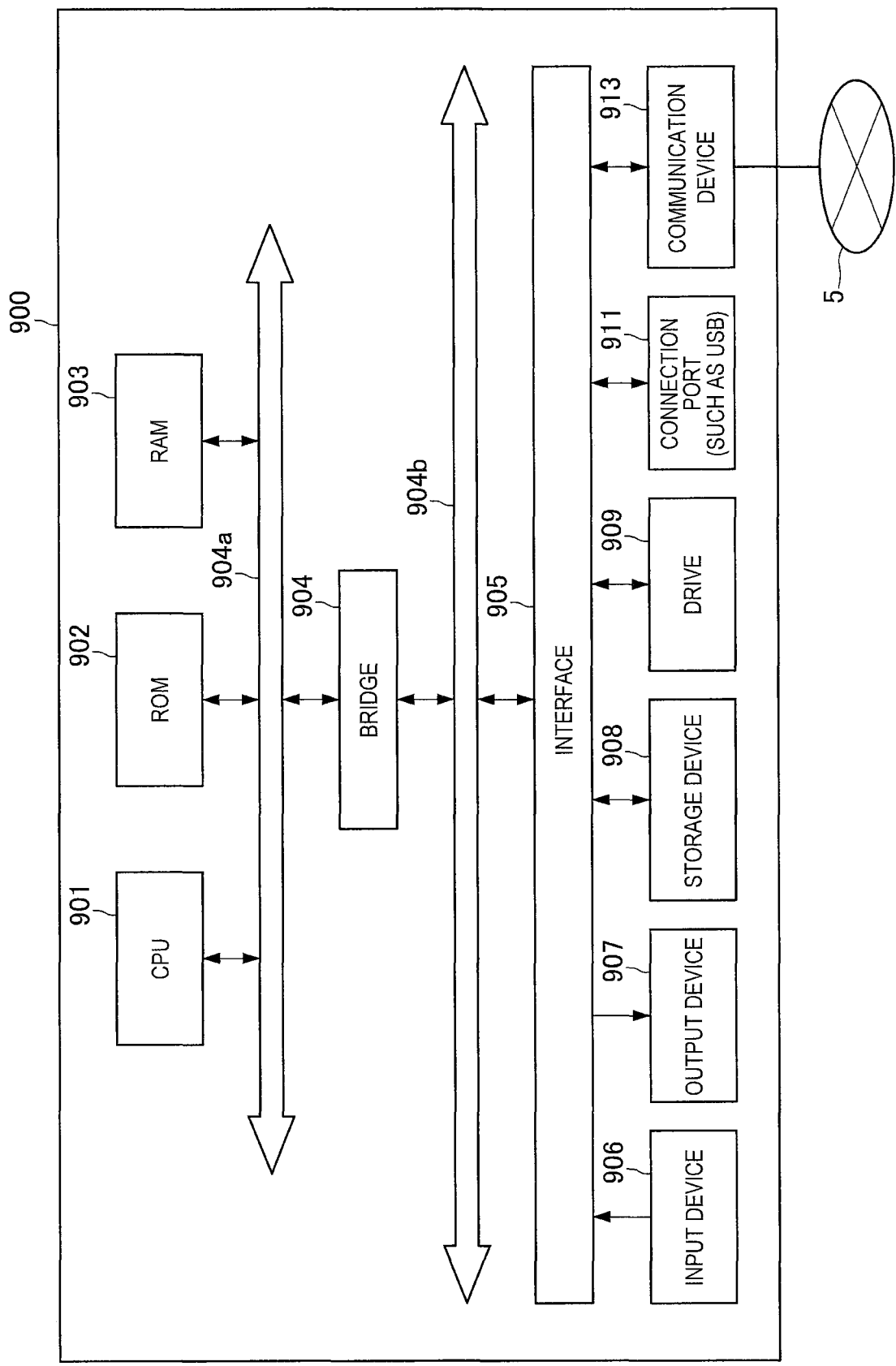
FIG. 18 is a hardware configuration diagram illustrating a hardware configuration of a functional unit that constitutes the information presentation system according to the present embodiment.

An exemplary hardware configuration of a functional unit that constitutes the information presentation system 100 according to the present embodiment is now described. FIG. 18 is a hardware configuration diagram illustrating the hardware configuration of a functional unit that constitutes the information presentation system 100 according to the present embodiment. Although FIG. 18 is described as an example of the hardware configuration of an information processing apparatus 900 including the respective functional units illustrated in FIG. 3, the similar configuration can be used in the case of an apparatus having only some of the functional units illustrated in FIG. 3.

As described above, the information processing apparatus 900 according to the present embodiment can be configured as a processing device such as a computer. The information processing apparatus 900 includes a central processing unit (CPU) 901, a read only memory (ROM) 902, a random access memory (RAM) 903, and a host bus 904a, as illustrated in FIG. 18. In addition, the information processing apparatus 900 includes a bridge 904, an external bus 904b, an interface 905, an input device 906, an output device 907, a storage device 908, a drive 909, a connection port 911, and a communication device 913.

The CPU 901 functions as an arithmetic processing unit and a control unit, and controls the overall operation in the information processing apparatus 900 in accordance with various programs. In addition, the CPU 901 can be a microprocessor. The ROM 902 stores programs, operation parameters, or the like used by the CPU 901. The RAM 903 temporarily stores a program to be used in the execution of the CPU 901 and stores parameters or the like that are appropriately changed in its execution. These are mutually connected through the host bus 904a composed of a CPU bus or the like.

The host bus 904a is connected to the external bus 904b, such as peripheral component interconnect/interface (PCI) bus, via the bridge 904. Moreover, the host bus 904a, the bridge 904, and the external bus 904b are not necessarily configured as independent components, but their functions can be equipped on one bus.

The input device 906 includes an input means that allows the user to input information, such as a mouse, a keyboard, a touch panel, a button, a microphone, a switch, and a lever, and includes an input control circuit for generating an input signal on the basis of an input by the user and outputting it to the CPU 901. The output device 907 includes, in one example, a display device such as a liquid crystal display (LCD) device, an organic light emitting diode (OLED) device, and a lamp, and an audio output device such as a loudspeaker.

The storage device 908 is an example of a storage unit of the information processing device 900 and is a device used to store data. The storage device 908 can include a storage medium, a recording device that records data in the storage medium, a reading device that reads data from the storage medium, a deletion device that deletes data recorded in the storage medium, and the like. The storage device 908 drives a hard disk, and stores programs executed by the CPU 901 and various data.

The drive 909 is a reader-writer for a storage medium, which is incorporated in the information processing apparatus 900 or externally attached thereto. The drive 909 reads information recorded on a removable recording medium such as a mounted magnetic disk, optical disk, magneto-optical disk, semiconductor memory, or the like, and outputs the information to the RAM 903.

The connection port 911 is an interface connected to an external device and, in one example, is a connection port with an external device capable of transmitting data by universal serial bus (USB) or the like. The communication device 913 is a communication interface constituted as a communication device or the like for the connection to a communication network 5. In addition, the communication device 913 can be a wireless local area network (LAN) compatible communication device, a wireless USB compatible communication device, or a wire communication device that performs wired communication.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a processing unit configured to present content to a user on a basis of sensor information acquired by a sensor configured to detect reaction of the user to a stimulus given to the user.

(2)

The information processing apparatus according to (1), in which the processing unit includes a model setting unit configured to set, for each user, a user model representing the reaction of the user to the stimulus on the basis of the sensor information, and a presentation processing unit configured to execute presentation processing of presenting the content to the user on a basis of the user model.

(3)

The information processing apparatus according to (2), in which a plurality of sense types are set depending on the reaction of the user to the stimulus, the model setting unit specifies one or the plurality of sense types corresponding to the reaction of the user on the basis of the sensor information and sets the sense type as the user model.

(4)

The information processing apparatus according to (3), in which the sense type includes at least a visual sense type, an auditory sense type, and a tactile sense type.

(5)

The information processing apparatus according to (3) or (4), in which the model setting unit, in a case where the plurality of sense types correspond to the reaction of the user, gives weighting to the corresponding sense types, and sets the sense types and the weighting as the user model.

(6)

The information processing apparatus according to any one of (2) to (5), in which a preset initial user model is initially set as the user model.

(7)

The information processing apparatus according to any one of (2) to (5), in which the presentation processing unit executes test processing of presenting test content to the user, and the model setting unit evaluates the reaction of the user on the basis of the sensor information in presenting the test content, and performs initial setting of the user model of the user on a basis of an evaluation result.

(8)

The information processing apparatus according to any one of (2) to (7), in which the model setting unit evaluates the reaction of the user on the basis of the sensor information in presenting the content by the presentation processing unit and updates the user model of the user on a basis of an evaluation result.

(9)

The information processing apparatus according to any one of (2) to (8), in which the presentation processing unit sets stimulus information based on the user model on an impression object used to give an impression to the user among objects included in the content, and executes processing of presenting the impression object on a basis of the stimulus information.

(10)

The information processing apparatus according to (9), in which the stimulus information is information used to scale up or down the impression object.

(11)

The information processing apparatus according to (9) or (10), in which the stimulus information is information used to blink the impression object.

(12)

The information processing apparatus according to any one of (9) to (11), in which the stimulus information is information used to add speech to the impression object to be displayed.

(13)

The information processing apparatus according to any one of (9) to (13), in which the stimulus information is information used to vibrate predetermined equipment together with presentation of the impression object.

(14)

The information processing apparatus according to any one of (9) to (13), in which the presentation processing unit changes the stimulus information to be set on a basis of a degree of importance of the impression object.

(15)

The information processing apparatus according to any one of (1) to (14), in which the processing unit presents the content to the user further on a basis of a user characteristic.

(16)

The information processing apparatus according to any one of (1) to (15), in which the sensor includes at least one of a biometric sensor configured to acquire biometric information of the user or an imaging device configured to capture an image of the user.

(17)

An information processing method including:

presenting content together with a stimulus;

detecting, by a sensor, reaction of a user to the stimulus given to the user; and estimating a dominant sense of the user on a basis of sense information acquired by the sensor.

(18)

A computer program causing a computer to function as an information processing apparatus including:
 a processing unit configured to present content to a user on a basis of sensor information acquired by a sensor configured to detect reaction of the user to a stimulus given to the user.

REFERENCE SIGNS LIST 10 impression object
100 information presentation system
110 sensors
111 biometric sensor
113 speech acquisition device
115 imaging device
120 model setting unit
130 reaction evaluation information storage unit
140 user model storage unit
141 sense type information
143 stimulus reaction history table
150 presentation processing unit
160 content storage unit
170 presentation unit

The invention claimed is:

1. An information processing apparatus, comprising:
  a sensor configured to:
    detect a first reaction of a user to a stimulus given to the user; and
    output first sensor information based on the detected first reaction of the user; and
  a processing unit configured to acquire the first sensor information from the sensor, wherein the processing unit includes:
    a model setting unit configured to:
      specify a sense type of the user among a plurality of sense types based on the acquired first sensor information, wherein
        each of the plurality of sense types represents a corresponding way of recognition of the stimulus by the user; and
      set a user model of the user based on the specified sense type, wherein the user model represents the first reaction of the user to the stimulus; and
    a presentation processing unit configured to control presentation of content to the user based on the set user model.

2. The information processing apparatus according to claim 1, wherein the processing unit is further configured to control the presentation of the content to the user further based on a user characteristic.

3. The information processing apparatus according to claim 1, wherein the sensor includes at least one of a biometric sensor configured to acquire biometric information of the user or an imaging device configured to capture an image of the user.

4. The information processing apparatus according to claim 1, wherein the specified sense type includes at least one of a visual sense type, an auditory sense type, or a tactile sense type.

5. The information processing apparatus according to claim 1, wherein the model setting unit is further configured to:
  in a case where the plurality of sense types corresponds to the first reaction of the user, give weight to the plurality of sense types; and
  set the user model of the user based on the weight to the plurality of sense types.

6. The information processing apparatus according to claim 1, further comprising a storage unit configured to store a specific initial user model as the user model.

7. The information processing apparatus according to claim 1, wherein
  the presentation processing unit is further configured to control presentation of test content to the user, and
  the model setting unit is further configured to:
    evaluate the first reaction of the user based on the acquired first sensor information,
      wherein the acquired first sensor information is based on the presentation of the test content; and
    execute initial setting of the user model of the user based on the evaluation of the first reaction of the user.

8. The information processing apparatus according to claim 1, wherein the model setting unit is further configured to:
  acquire second sensor information from the sensor based on the presentation of the content to the user;
  evaluate a second reaction of the user based on the acquired second sensor information; and
  update the user model of the user based on the evaluation of the second reaction of the user.

9. The information processing apparatus according to claim 1, wherein the presentation processing unit is further configured to:
  set, based on the user model, stimulus information on an impression object of a plurality of objects included in the content, wherein
    the impression object is for provision of an impression to the user; and
  control presentation of the impression object based on the set stimulus information.

10. The information processing apparatus according to claim 9, wherein the stimulus information is information to one of scale up or scale down the impression object.

11. The information processing apparatus according to claim 9, wherein the stimulus information is information to blink the impression object.

12. The information processing apparatus according to claim 9, wherein the stimulus information is information for addition of speech to the impression object to be displayed.

13. The information processing apparatus according to claim 9, wherein the stimulus information is information for vibration of a specific equipment together with the presentation of the impression object.

14. The information processing apparatus according to claim 9, wherein the presentation processing unit is further configured to change the stimulus information based on a degree of importance of the impression object.

15. An information processing method, comprising:
  in an information processing apparatus that includes a sensor and a processing unit, wherein the processing unit includes a model setting unit and a presentation processing unit:
    detecting, by the sensor, a reaction of a user to a stimulus given to the user;
    outputting, by the sensor, sensor information based on the detected reaction of the user;
    acquiring, by the processing unit, the sensor information from the sensor;
    specifying, by the model setting unit, a sense type of the user among a plurality of sense types based on the acquired sensor information, wherein each of the plurality of sense types represents a corresponding way of recognition of the stimulus by the user;

setting, by the model setting unit, a user model of the user based on the specified sense type, wherein the user model represents the reaction of the user to the stimulus; and controlling, by the presentation processing unit, presentation of content to the user based on the set user model.

16. A non-transitory computer-readable medium having stored thereon computer-executable instructions that, when executed by an information processing apparatus, cause the information processing apparatus to execute operations, the operations comprising:

detecting, by a sensor of the information processing apparatus, a reaction of a user to a stimulus given to the user;

outputting, by the sensor, sensor information based on the detected reaction of the user;

acquiring, by a processing unit of the information processing apparatus, the sensor information from the sensor;

specifying, by a model setting unit of the processing unit, a sense type of the user among a plurality of sense types based on the acquired sensor information, wherein each of the plurality of sense types represents a corresponding way of recognition of the stimulus by the user;

setting, by the model setting unit, a user model of the user based on the specified sense type, wherein the user model represents the reaction of the user to the stimulus; and controlling, by a presentation processing unit of the processing unit, presentation of content to the user based on the set user model.

* * * * *